United States Patent
Jacobson et al.

(10) Patent No.: US 8,369,916 B2
(45) Date of Patent: Feb. 5, 2013

(54) OPTICAL FIBER CONNECTOR

(75) Inventors: Ross W. Jacobson, Hillsborough, NC (US); Alexander G. Lastovich, Raleigh, NC (US); Lawrence A. Monahan, Willow Spring, NC (US); Edward P. Browka, Troy, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 564 days.

(21) Appl. No.: 12/527,999

(22) PCT Filed: Feb. 25, 2008

(86) PCT No.: PCT/US2008/054834
§ 371 (c)(1),
(2), (4) Date: Dec. 23, 2009

(87) PCT Pub. No.: WO2008/103972
PCT Pub. Date: Aug. 28, 2008

(65) Prior Publication Data
US 2010/0099965 A1    Apr. 22, 2010

Related U.S. Application Data

(60) Provisional application No. 60/891,411, filed on Feb. 23, 2007.

(51) Int. Cl.
*A61B 5/00* (2006.01)
(52) U.S. Cl. ........................................ 600/342; 600/344

(58) Field of Classification Search ................... 600/339, 600/341, 342, 344, 478
See application file for complete search history.

(56) References Cited

U.S. PATENT DOCUMENTS

| 7,792,561 B2 * | 9/2010 | Alarcon et al. ............... 600/317 |
| 2005/0113658 A1 * | 5/2005 | Jacobson et al. .............. 600/342 |
| 2008/0146902 A1 * | 6/2008 | Hacker et al. ................. 600/342 |

FOREIGN PATENT DOCUMENTS

| WO | WO 2004082468 A2 * | 9/2004 |
| WO | WO 2006044973 A1 * | 4/2006 |

* cited by examiner

*Primary Examiner* — Christopher Mahoney
(74) *Attorney, Agent, or Firm* — Morgan, Lewis & Bockius LLP

(57) ABSTRACT

An optical connector device is disclosed for optically connecting a biosensor wearable on the body of a patient to a reader outside of the body of the patient. The device comprises a base disk to be worn on the body of a patient. The base disk has a needle attached thereto and the needle houses a first fiber defining a first optical conduit. The distal end of the needle is insertable into the body of the patient, and a portion of the proximal end of the needle remains outside of the body of the patient when the device is worn. The device also comprises a connector housing a second fiber defining a second optical conduit.

67 Claims, 15 Drawing Sheets

OPTICAL FIBER CONNECTOR

BACKGROUND OF THE INVENTION

Related Applications

This application is a U.S. National Phase Application of International Application PCT/US2008/054834, filed Feb. 25, 2008, which claims the benefit of U.S. Provisional Application No. 60/891,411 filed Feb. 23, 2007, all of which are incorporated herein by reference in their entireties.

1. Field of the Invention

The present invention generally relates to an optical fiber connector to allow for a wearable sensor that can be quickly disconnected from an optical reader.

2. Description of the Related Art

Optical fiber connectors, or splices, are essential parts of optical fiber communications systems. Connectors may be used to join lengths of optical fiber to form longer lengths or to connect an optical fiber to an active device, such as a radiation source, a detector, or a repeater, or to a passive device, such as switch or an attenuator.

Generally, an optical fiber connector must meet at least two requirements. First, it must couple or join two optical fibers with minimum insertion loss. Second, it must provide mechanical stability and protection to the junction between the optical fibers in the working environment. Achieving low insertion loss in coupling two optical fibers is generally a function of the alignment of the optical fiber ends, the width of the gap between the ends, and the optical surface condition of the ends. Stability and junction protection is generally a function of connector design, such as, for example, the minimization of differential thermal expansion or vibration effects.

A further consideration in connector design is the relative ease of installation of the connector. It is desirable that a sought-after connector be capable of being installed within a relatively short period of time without requiring special skills or manipulations not easily carried out in the field.

Current optical fiber connectors are not suitable for the medical field. For example, current optical fiber connector designs are typically used for fiber optic networks and are not designed with a low profile elevation. That is, the extended length of a conventional fiber optic connector provides excellent alignment between connected fibers but would be inconvenient for a device worn by a patient.

Also, conventional connectors used in the communications field are quite expensive, typically greater than $30 per connector. Furthermore, additional complications are introduced in a connector design to mate different diameter fibers, which may be necessary for certain medical applications. Finally, a quick connection time without requiring special skill is essential for medical applications, where a patient would connect/disconnect the connector.

Accordingly, there is a need for an optical fiber connector suitable for medical applications.

SUMMARY OF THE INVENTION

A first aspect of the invention is an optical connector device for optically connecting a biosensor wearable on a body of a patient to a reader outside of the body of the patient. The device comprises a base disk configured and dimensioned to be worn on the body of a patient. The base disk has a needle attached thereto and the needle houses a first fiber defining a first optical conduit. The needle has a proximal end and a distal end, and the distal end of the needle is insertable into the body of the patient and is configured to remain inside of the body of the patient when the device is worn. At least a portion of the proximal end of the needle remains outside of the body of the patient when the device is worn. The device also comprises a connector housing a second fiber defining a second optical conduit. The connector is configured and dimensioned to couple with the base disk to position the first fiber in optical proximity to the second fiber and align the first optical conduit with the second optical conduit such that an optical signal may be transmitted from the first optical conduit to the second optical conduit. A sensor element is positioned on the distal end of the needle.

The sensor element may be configured to transmit an optical signal in response to a target analyte. The connector can be removably coupleable to the base disk.

A removable cover can be positionable over the distal end of the needle for protecting the sensor element when the sensor is not in use. In one variation, the cover comprises a hydration chamber to keep the sensor element wet.

A depth limiting device may be attached to the base disk wherein the depth limiting device limits the depth that the distal end of needle may be inserted into the body of the patient. The base disk may include an adhesive that is configured and dimensioned to be worn on the exterior skin of the patient. The base disk may have a general flat shape with a generally circular perimeter. The needle may be fixed to the base disk with glue, and a glue well may be positioned on the distal side of the base disk to fix the needle to the base disk. The base disk may have a height between about 0.1 cm and about 2 cm.

In one variation, the connector has a connector body with a pair of arms extending laterally therefrom. A fiber pigtail may extend from the proximal end of the connector or the connector may be integrally formed with a wearable optic reader. The connector body may have a general U shape with sidewalls extending distally from a top wall portion. At least one prong member may extend laterally outward from the sidewalls, wherein the prong member is configured and dimensioned to engage a portion of the receptacle to mate the connector with respect to the base disk. In one variation, a portion of the pair of arms are sloped downward. The arms may be generally flexible such that the arms may be squeezed together by a user to insert or remove the connector from the base disk.

When the connector is coupled to the base disk, the connector may be resiliently biased against the base disk to hold the first and second fibers in close proximity. The base disk and connector may be made from plastic. The total height of the device may be less than about 1 cm. The first optical conduit has a first diameter and the second optical conduit has a second diameter. The first and second diameters may be substantially the same size or the first and second diameters may have different sizes. The connector may be keyed to align with the base disk to prevent relative rotation between the connector and base disk upon coupling.

A second aspect of the invention is a method of optically connecting a biosensor wearable on a body of a patient to a reader outside of the body. The method includes attaching a base disk to the body of the patient, the base disk having a needle attached thereto, the needle housing a first fiber defining a first optical conduit, and the needle comprising a proximal end and a distal end, wherein the distal end of the needle is inserted into the body of the patient and is configured to remain inside of the body of the patient with at least a portion of the proximal end of the needle remaining outside of the body of the patient when the device is worn. The method also includes coupling a connector with the base disk; the connector housing a second fiber defining a second optical conduit, wherein the connector is configured and dimensioned to couple with the base disk to position the first fiber in optical proximity to the second fiber and align the first optical conduit with the second optical conduit such that an optical signal may be transmitted from the first optical conduit to the second optical conduit.

The method may also include decoupling the connector from the base disk, and coupling another connector to the base disk. The attaching of the base disk to the body of the patient may include inserting the distal end of the needle such that the needle is substantially perpendicular to the patient's skin. The coupling of the connector to the base disk may include aligning the connector so that the second fiber is substantially aligned with respect to the first fiber and/or aligning the connector so that a center of the connector is provided over a center of the base disk.

BRIEF DESCRIPTION OF THE DRAWINGS

The invention will be more readily understood with reference to the embodiments thereof illustrated in the attached figures, in which.

DETAILED DESCRIPTION OF THE EXEMPLARY EMBODIMENTS

Exemplary embodiments of the invention will now be described. The following detailed description of the invention is not intended to be illustrative of all embodiments. In describing exemplary embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

Figure 1:
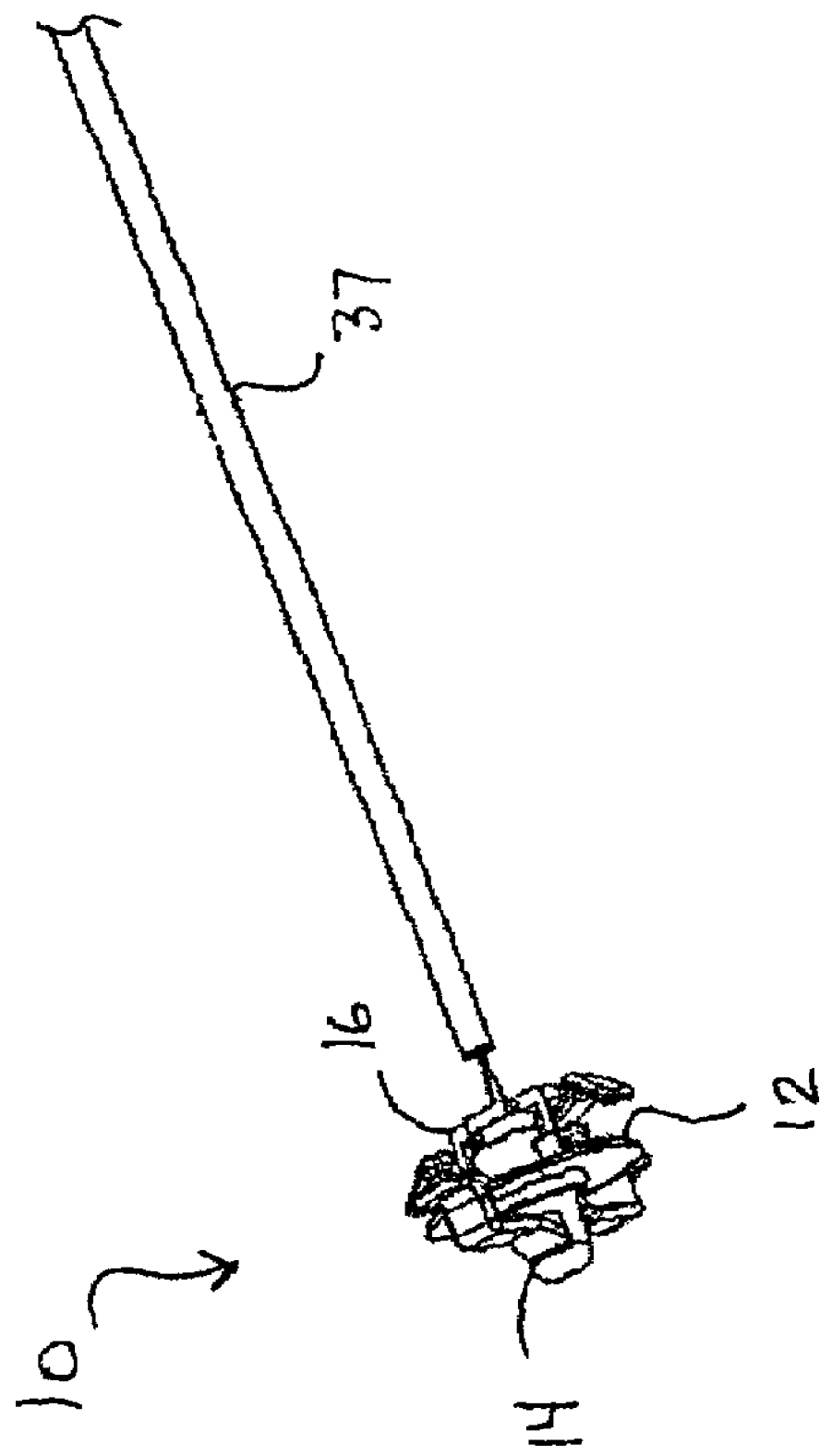
FIG. 1 is an perspective view of a first exemplary embodiment of an assembled optical fiber connector device.
Figure 2:
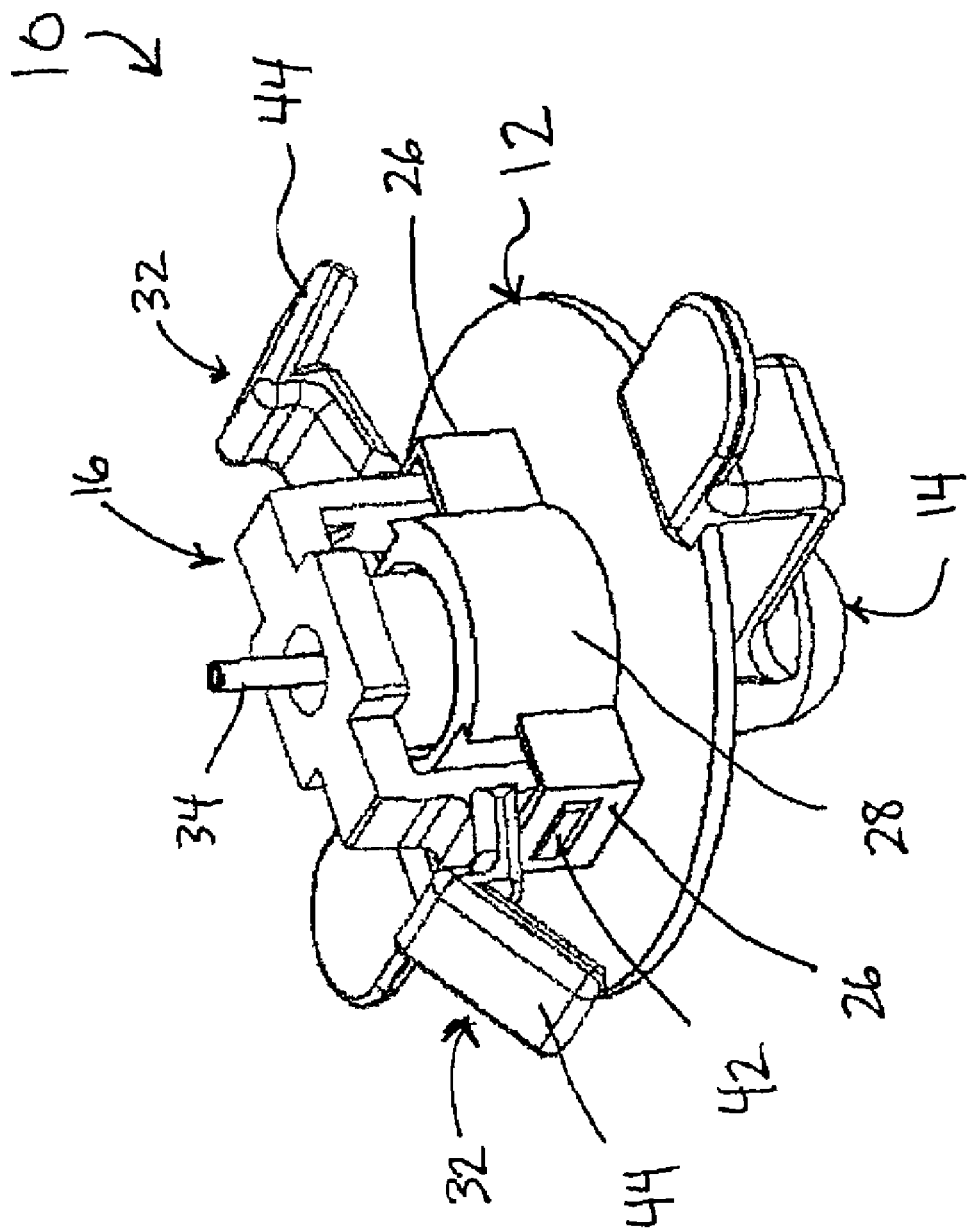
FIG. 2 is an enlarged view of the device.
Figure 7:
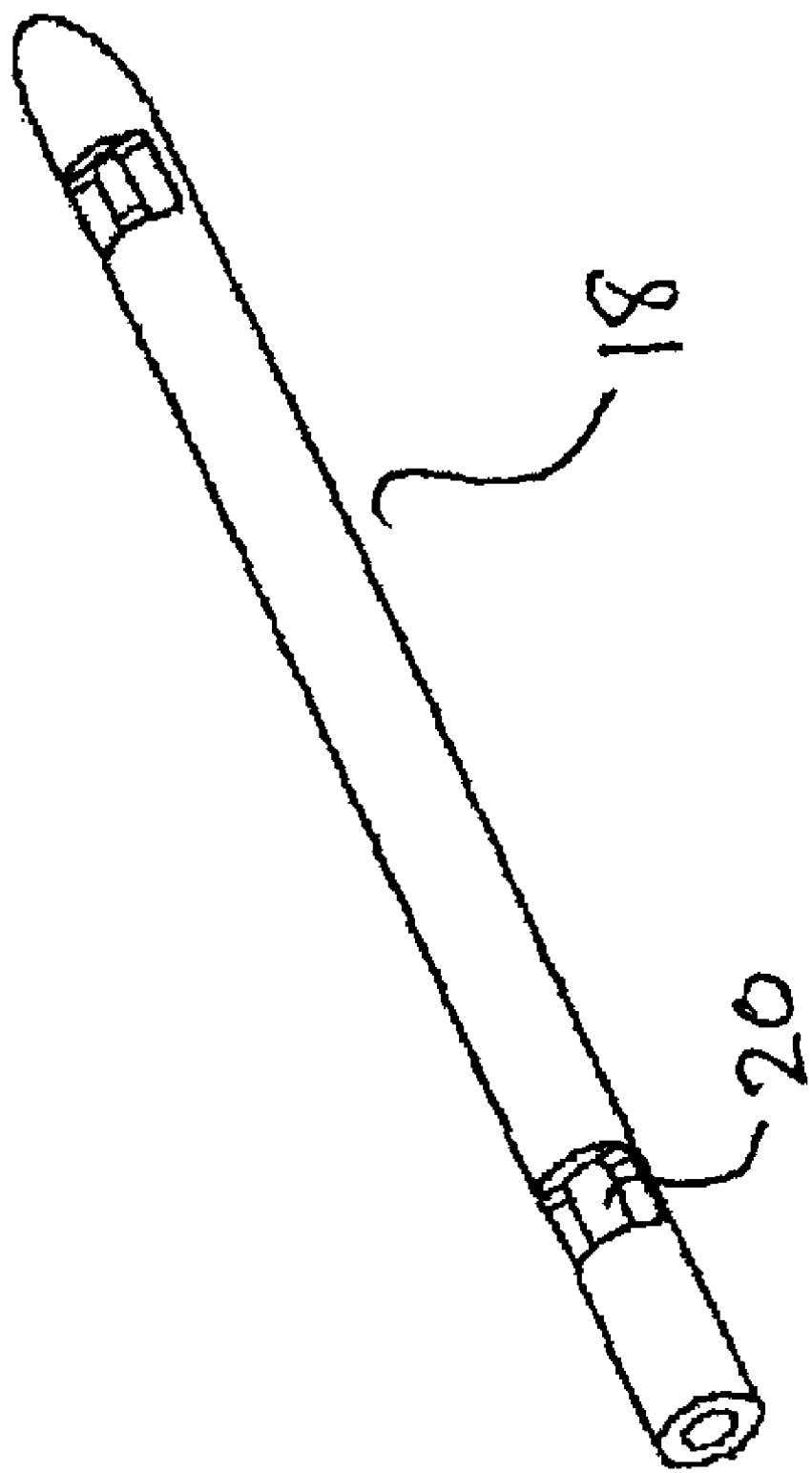
FIG. 7 is a perspective view of a needle of the first exemplary embodiment.

Referring now to FIGS. 1 and 2, a first exemplary embodiment of an optical connector device 10 according to the present invention is shown. In general, the optical connector device 10 includes a wearable sensor device that can be disconnected from its optical reader during non-experimental durations (i.e., non data acquisition periods). The optical connector device 10 generally includes a button assembly or base disk 12, a removable cover 14, and a connector 16. In general, a needle 18 is attached to the base disk 12 and houses a first fiber 20 (shown in FIG. 3 and FIG. 7) and acts as an optical conduit through which light signals may pass.

A sensor element, including sensor chemistry, is positioned on the distal or patient end of the fiber 20 within the needle 18. Representative sensor chemistry and sensor element configurations that may be utilized are disclosed in co-pending U.S. Patent Publication No. US 2005/0113658, entitled "Fiber Optic Device for Sensing Analytes and Method of Making Same," the entire content of which is incorporated herein by reference.

In the first exemplary embodiment, as shown in FIG. 2, the removable cover 14 may be positioned over the distal end of the needle 18 to protect the sensor element prior to use. The cover 14 may also function as a hydration chamber for chemistry that may need to be kept wet.

In this exemplary embodiment, the base disk 12, the cover 14, and the connector 16 may be made of moldable plastic. In alternate embodiments, any other suitable material may be used.

The base disk 12 is configured and dimensioned such that it may be worn by a patient. That is, the needle 18 may be inserted into the skin of a patient so that the sensing element resides in either the intradermal or subcutaneous space. In this exemplary embodiment, the needle 18 may be inserted substantially perpendicular to the patient's skin; however, in alternate embodiments, the needle 18 may be inserted at any other suitable angle with respect to the skin of a patient. In the exemplary embodiment, the needle 18 is fixedly mounted to the base disk 12 such that a controlled insertion depth may be obtained. In this regard, in this exemplary embodiment, the needle 18 extends into the skin of a patient a distance between about 0.1 mm to about 10 mm, or preferably between about 1 mm to about 5 mm. The body of the base disk 12 may be designed to accommodate different needle or cannula sizes, as desired. Accordingly, several different fiber sizes and/or combinations of fiber sizes may be utilized. For example, in this exemplary embodiment, the needle 18 is a 25 Ga cannula.

Figure 3:
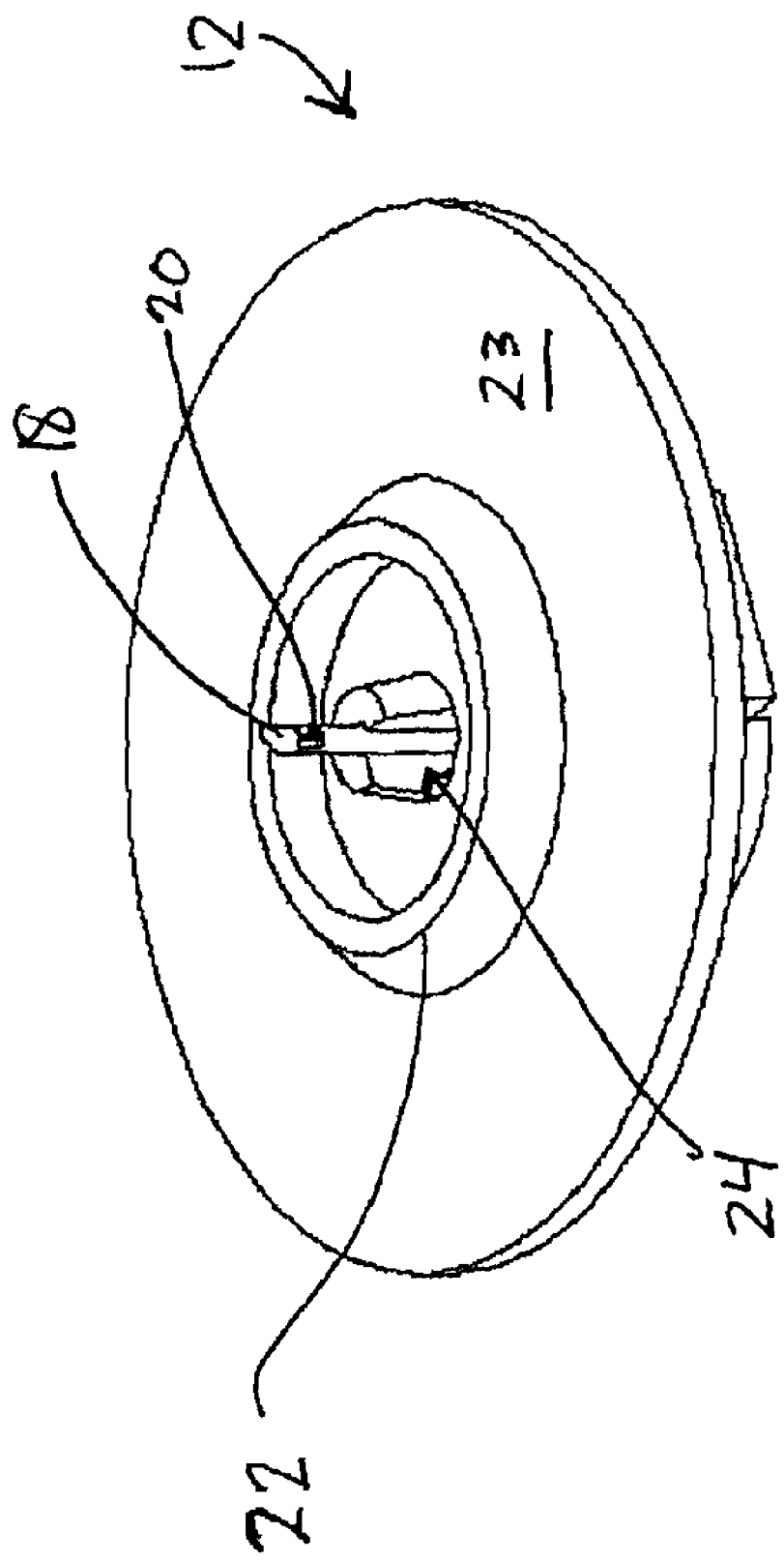
FIG. 3 is a perspective view of a base disk of the first exemplary embodiment.

FIG. 3 shows a distal or underside of the base disk 12 of this exemplary embodiment. As shown in FIG. 3, in the exemplary embodiment base disk 12 has a general flat disk shape with a generally circular perimeter. A circular or frusto-conical rim 22 is spaced radially inward from the perimeter and protrudes in a distal direction from the distal surface 23 of disk 12. The size and shape of the perimeter of base disk 12 in combination with the dimensions and configuration of protruding rim 22 generally promotes good sensor depth and limits rock and motion of the sensor relative to the body tissue when the needle 18 is inserted into a patient. A glue well 24 for fixing needle 18 to the body of disk 12 is positioned on the distal side of disk 12 adjacent a central opening in disk 12 to fix needle 18 to disk 12. The glue well 24 is spaced from the connector 16 in order to reduce the chance of adhesive migration into the fiber coupling area.

As best seen in FIG. 2, the proximal, or back side, of base disk 12 generally comprises openings or receptacles 26 adjacent a central collar portion 28. The receptacles 26 receive and/or accommodate prong members 42 of the connector 16. In general, the base disk 12 has a low profile compared to the assembled connector device 10, which greatly improves the wearability of the optical fiber device 10. For example, the base disk 12 may have a height between about 0.1 cm and about 2 cm. In this exemplary embodiment, the collar portion 28 is chamfered or rounded along the internal portion to facilitate alignment, orientation and/or insertion of connector 16. This can further enable the user to connect the fiber by tactile feedback. Therefore, visual feedback is not necessary and a connection can be provided on locations of the patient's body that the patient cannot see.

Figure 4:
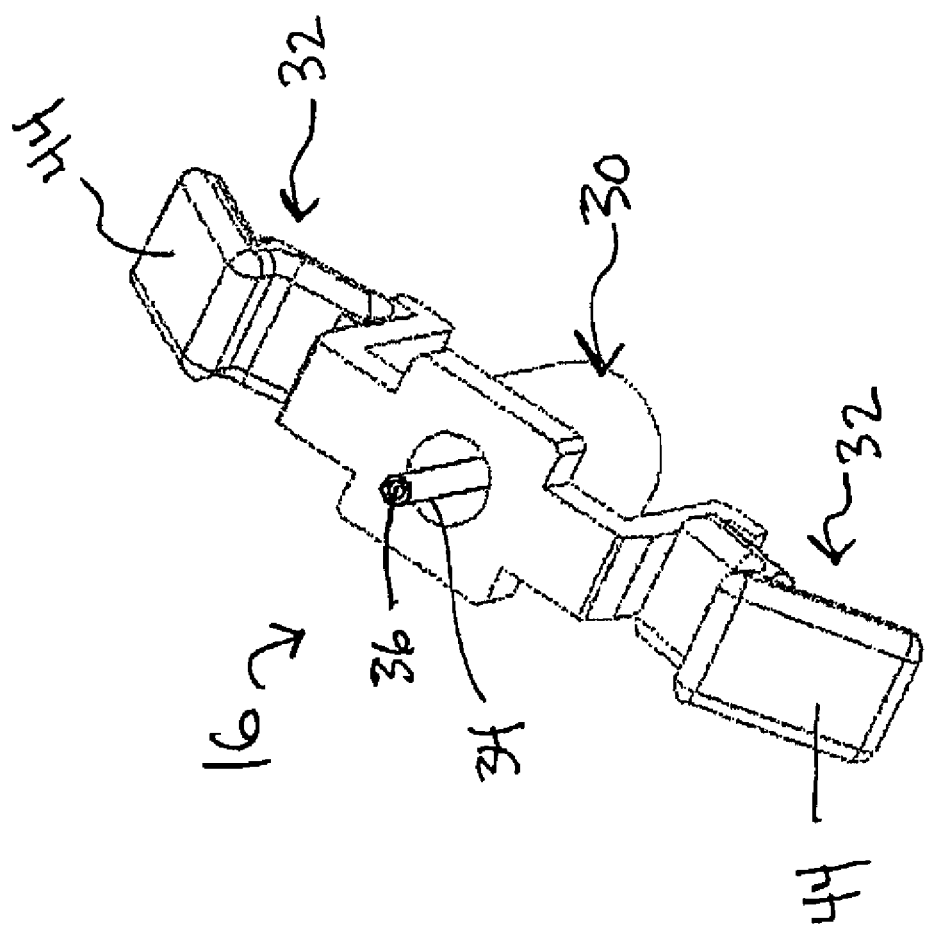
FIG. 4 is a perspective view of a connector of the first exemplary embodiment.

Referring to FIG. 4, the connector 16 generally includes a connector body 30 with a pair of tabs or arms 32 extending laterally therefrom. A tube or cannula 34 extends through a connector body 30 and houses a portion of a read fiber or second fiber 36. The fiber 36 acts as an optical conduit through which light signals may pass.

As shown in FIG. 1, a fiber pigtail 37 may extend from the proximal end of connector 16. Therefore, the connector 16 is connected to and communicates with an external reader (not shown). Alternatively, the connector 16 can be integrally formed with a wearable optic reader (not shown).

Figure 5:
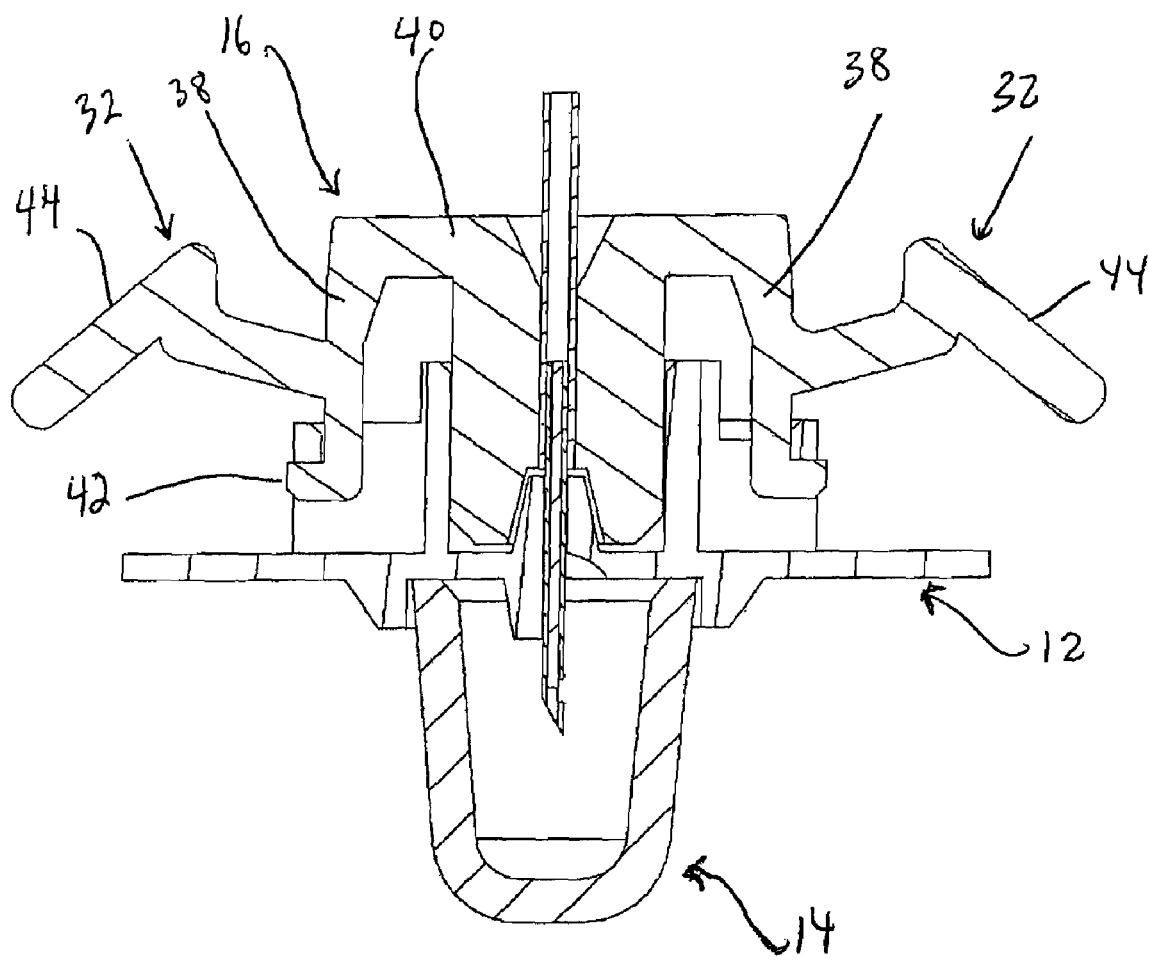
FIG. 5 is cross-sectional view of the device.
Figure 6:
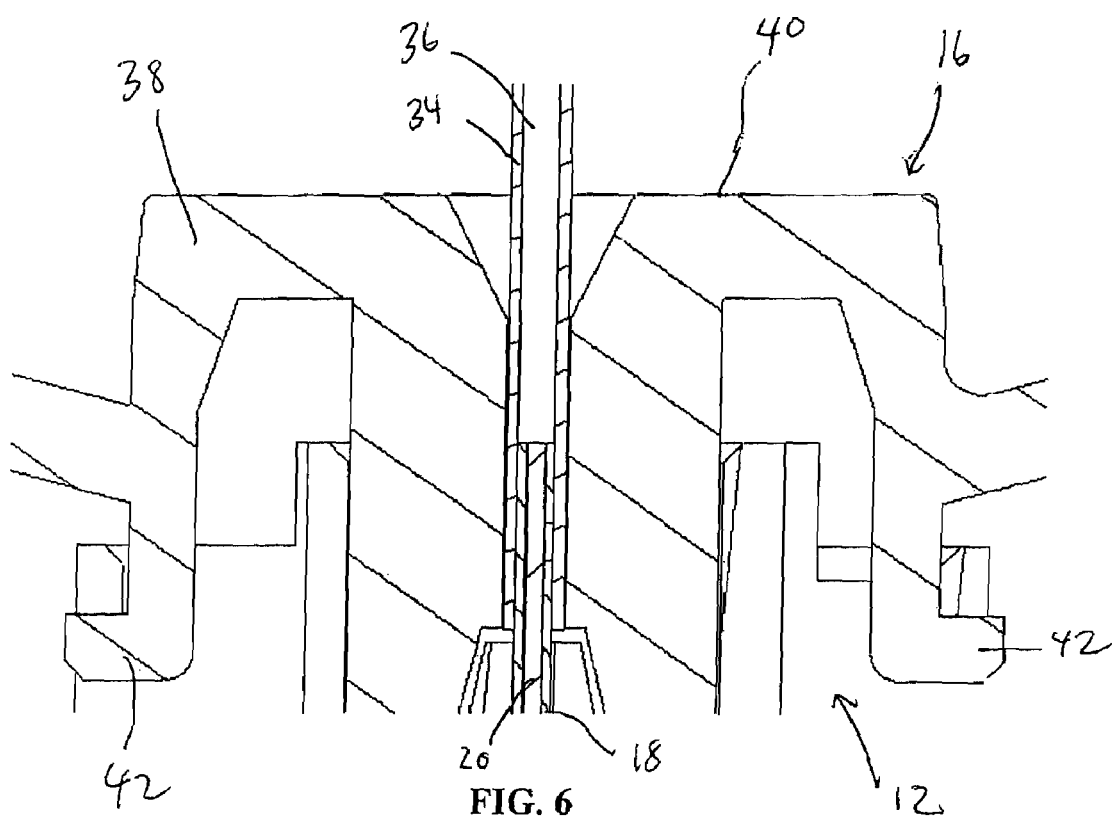
FIG. 6 is an enlarged cross-sectional view of the device.

As best seen in FIGS. 5 and 6, the connector 16 has a general U or horseshoe shape with sidewalls 38 extending distally from a top wall portion 40 of the connector 116. Prong members 42 extend laterally outward from the distal ends of sidewalls 38 and are configured and dimensioned to engage a portion of receptacles 26 of the base disk 12, therefore snapping or holding the connector 16 in place with respect to base disk 12. As can be seen in FIG. 2, the outer portions 44 of arms 32 are sloped downward creating a sleek profile that reduces the chance of accidental pullout caused by, for example, clothing or other environmental features that may be caught on the device. The arms 32 of the connector 16 are generally flexible such that the arms may be squeezed together by a user or pushed downward and radially inward to move the prongs 42 radially inward and provide clearance to insert or remove connector 16 from base disk 12. When the arms 32 are released, the prong members 42 resiliently snap fit into the receptacles 26 on base disk 12, thus attaching the connector 16 to the base disk 12. The snap features of the connector provide a positive feed back snap (tactile and auditory) to notify the user of proper engagement.

In this exemplary embodiment, the configuration of the pair of arms 32 requires simultaneous application of force on the two outer portions 44 in order to release the connector 16 from the base disk 12. In this regard, inadvertent release of the connector may be prevented. In this exemplary embodiment, the coupling of the connector 16 to the base disk 12 includes aligning the connector 16 so that a center of the connector 16 is provided over a center of the base disk 12. In this way, the base disk fiber 18 is substantially aligned with respect to the connector fiber 36.

The sidewalls 38 and prongs 42 of the connector 16 are resiliently biased in a radially outward direction when the connector 16 is attached to the base disk 12 such that a net downward or distal force is applied to connector 16. In this regard, the downward force of the connector 16 against the base disk 12 holds the fiber faces tight or in close proximity.

Figure 8:
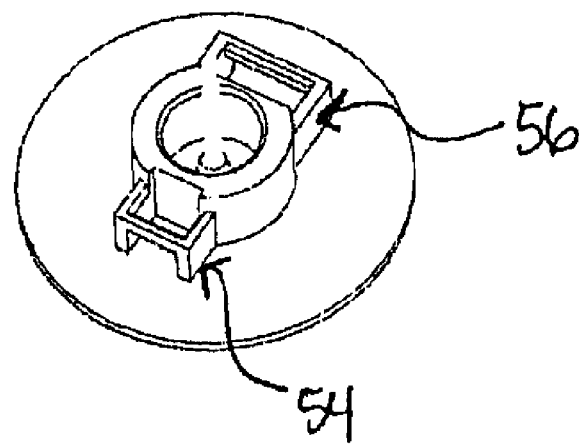
FIGS. 8 and 9 are perspective views of a modification of the first exemplary embodiment of the connector device.
Figure 9:
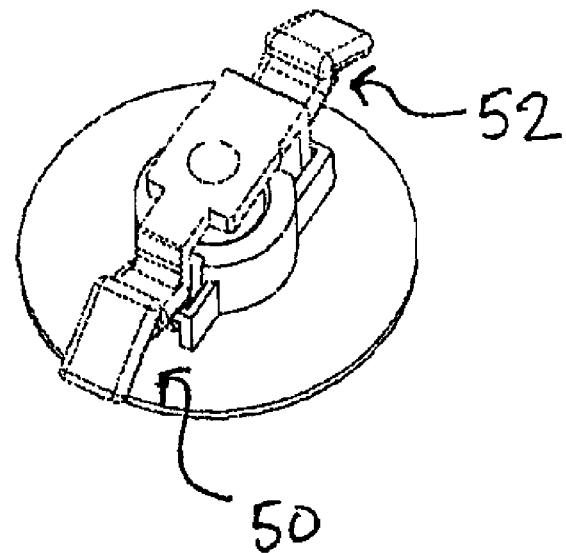

In a modification of the first exemplary embodiment, shown in FIGS. 8 and 9, one of the snap fastener arms 50 and a corresponding receptacle 54 may have distinctly different shapes and/or sizes with respect to opposing snap fastener arm 52 and corresponding receptacle 56. This limits the rotational alignment of the fibers.

In this exemplary embodiment, the cannula 34 of the connector 16 is an 18 Ga cannula, however, in alternate embodiments, cannula 34 may be of any suitable gauge as desired.

The pigtail fiber 37 may include an SMA (SubMiniature version A) connector adjacent a proximal end for attachment to the reader.

FIGS. 5 and 6 are cross-sectional views of the first exemplary embodiment of the optical connector device 10, showing the connector 16 attached to the base disk 12. In this exemplary embodiment, a 25 Ga needle 18 is installed in the base disk 12, and a 21 Ga cannula 34 is installed in the connector 16. As can be seen in this exemplary embodiment, the 25 Ga needle 18 of the disk 12 fits radially within the 25 Ga cannula 34 of the connector 16. A 400 um fiber 36 (i.e., fiber with 400 um core) in the 21 Ga cannula 34 can be pressed tightly against the top or proximal end of a 25 polished 200 um fiber 20 (i.e., fiber with 200 um core) within the 25 Ga needle 18. In this exemplary embodiment, the fibers can be polished flush with the blunt end of the cannula, and in other exemplary embodiments the fiber may be recessed slightly, with an index matching gel provided within the recess, to create the desired fiber-to-fiber fit. In another exemplary embodiment, the cannula 34 of connector 16 may include a tapered or flared outward distal end to facilitate alignment of connector 16. In general, the polished fiber surfaces provide transmission of signal therethrough when there is intimate contact between the two fibers. Moreover, additional optical components including, but not limited to, filters, lenses and/or index matching materials may be interposed between the fibers.

The ease of connection/disconnection and interchangeability of any base disk 12 with any connector 16 can allow multiple sensors to be read by a single reader, because the reader or the second fiber 36 can easily be switched. In the first exemplary embodiment, a 400 um fiber may be coupled to a 200 um fiber. That is, because the fiber 20 is contained within a 25 Ga needle 18, a near line-to-line fit between the fibers 20, 36 can be provided.

However, the invention is not limited in this respect and almost any size pairing of fibers as desired can be used. For example, modifications of this exemplary embodiment include a 200 um to 200 um fiber connection or a 400 um fiber to 400 um fiber connection. Moreover, a base disk 12 according to the exemplary embodiment can be coupled with different connectors. For example, the connector 16 with a 400 um fiber 36 shown in FIG. 6 can be decoupled from the base disk 12 and another connector (not shown), which could include, for example, a 200 um fiber, can be instead coupled to the base disk 12. This allows the same base disk 12 to remain attached to the patient when different optic readers are used or if a connector were to need to be replaced due to breakage or other loss.

The needle 18 may be made from steel, ceramic, glass or any other suitable material. In general, cannula 34 may include a tubular body that could be made from any optically opaque, suitably stiff material. Alternatively, the base disk may be mated with a connector integrated in the body of the external optical reader.

The components are assembled and affixed in such a way that a guaranteed fiber-to-fiber contact is established. The flex of the side walls 38 and connector arms 32 provides the theoretical interference needed to establish this face-to-face contact. In some embodiments, the fiber faces have a guaranteed contact because the flex of the side walls 38 is loaded in such a way that prongs 42 bias the fiber faces together. The amount of said load is determined by the location of the cannula and/or fiber faces when they are affixed during assembly. As one of skill in the art will appreciate, the amount of load is thus infinitely customizable within the limits of the material of connector 16.

In the operation of the first exemplary embodiment of the optical connector device 10, the cover 14 is removed from the base disk 12, thus exposing the distal end of the needle 18. Then, the disk 12 is placed on the patient such that needle 18 penetrates the patient's skin. The disk 12 may be secured in place on the patient by using, for example, an adhesive, tape, or other securing means. The connector 16 is then placed into the back or proximal end of disk 12 until it snaps into place. This establishes an optical connection from the reader to the sensor/chemistry placed at the distal end of needle 18. When the desired readings have been taken, the arms 32 on the connector 16 may be squeezed radially inward to separate the connector 16 from the base disk 12. This process can be repeated as many times as desired to, for example, take multiple readings over long periods of time. In this regard, the design of the optical connector device 10 allows for the portion of the device that remains attached to the patient to be a low profile component as opposed to having a pigtail fiber permanently connected thereto or another taller connector which may be more easily dislodged or removed.

In another implementation of the device, the base disk 12 is configured and dimensioned to be used in combination with a ballistic inserter to aid in skin penetration of the needle or cannula. Because disk 12 can be loaded and fired free of the interference of a fiber optic tether or fiber pigtail, repeatability and velocity of the insertion may be improved or optimized. The size and shape profile of the body lends itself to be used with existing auto inserter devices, such as, for example, the auto inserter sold by Minimed.

Figure 10:
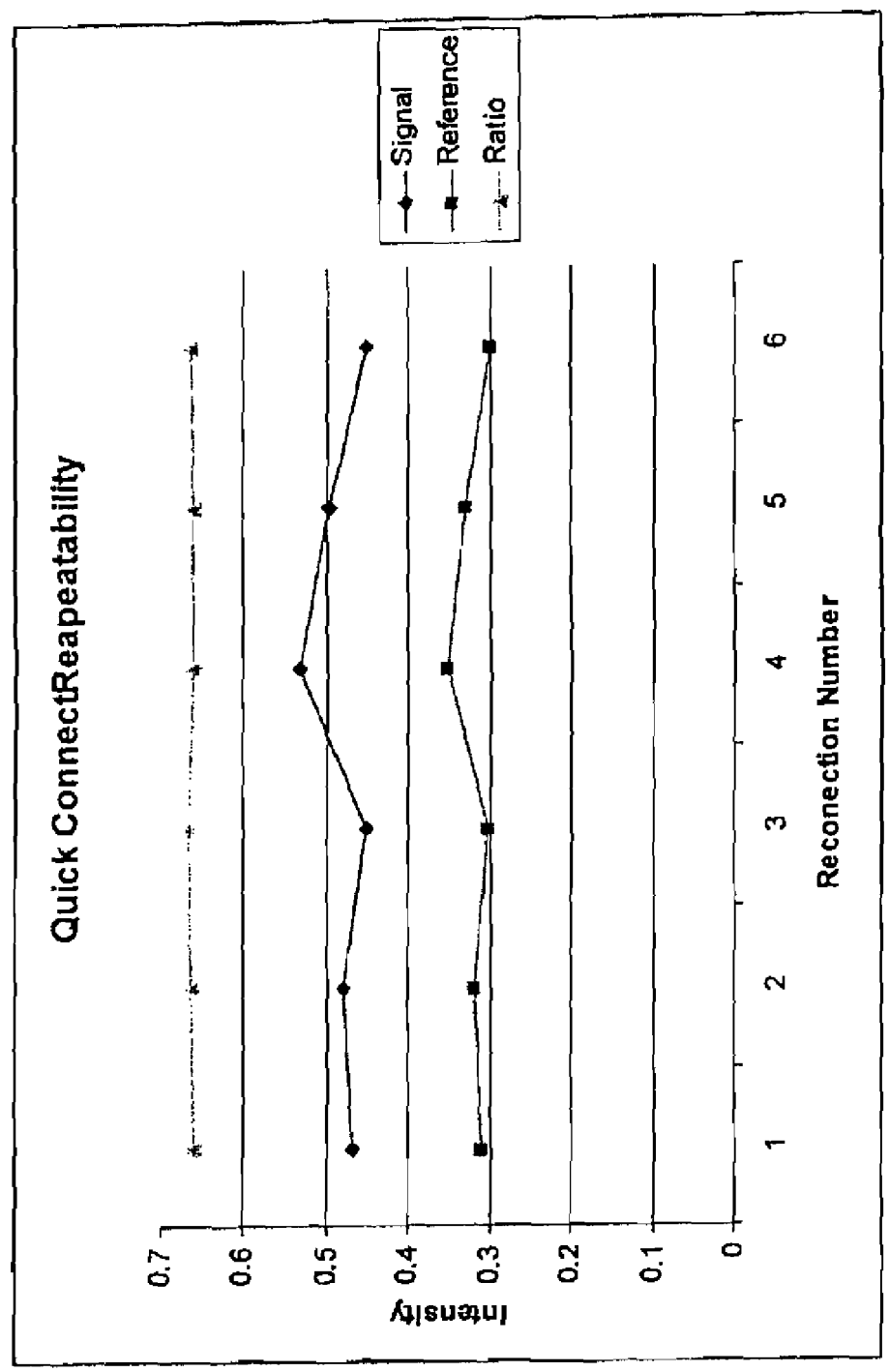
FIG. 10 is a chart depicting exemplary repeatability results of optical readings taken over time after multiple disconnections and reconnections of the connector to the base of the first exemplary embodiment.

FIG. 10 is a graphical presentation depicting a signal level as measured in absolute intensity upon a number of disconnections/reconnections of the base disk and connector according to the first exemplary embodiment of an optical fiber connector device. This figures shown that the signal level as measured in absolute intensity does not vary outside proscribed limits.

Figure 11:
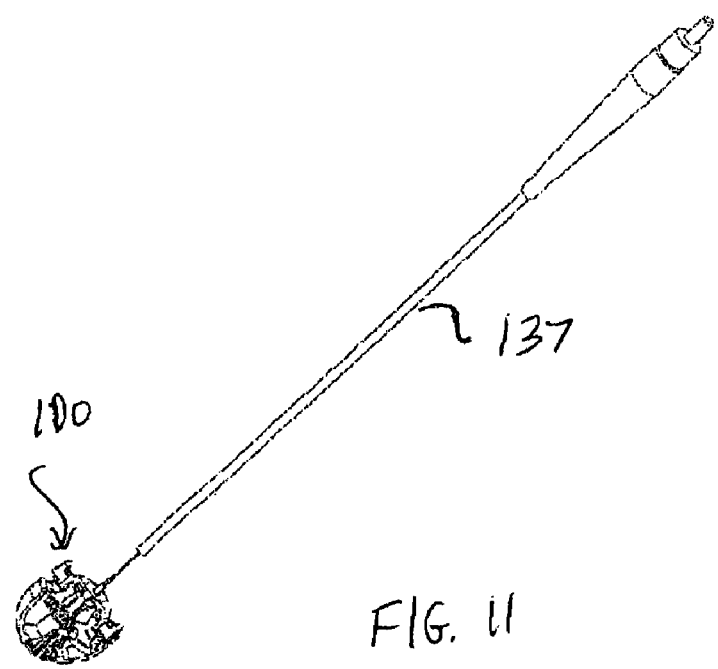
FIGS. 11 and 12 show a second exemplary embodiment of an optical connector device.
Figure 12:
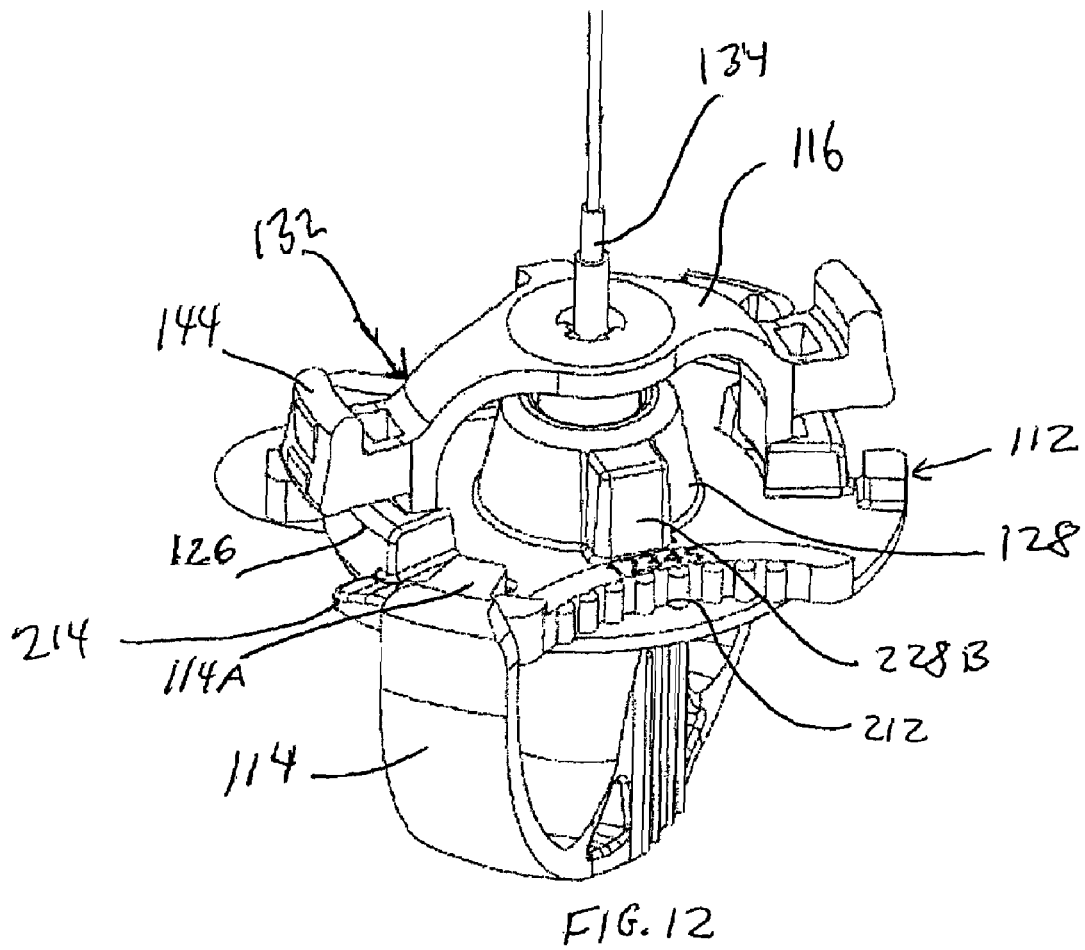

FIGS. 11 and 12 show a second exemplary embodiment of an optical connector device 100 according to the present invention. Like the first exemplary embodiment, the optical connector device 100 of the second exemplary embodiment includes a wearable sensor device that can be disconnected from its optical reader during non-experimental durations. Moreover, the materials and structure of the second exemplary embodiment are similar to that of the first embodiment in many respects. The description of the second exemplary embodiment will focus on the differences between these two exemplary embodiments.

Like the optical connector device 10, the optical connector device 100 generally includes a base disk or button 112, a removable cover 114, and a connector 116. A sensor element is positioned on the distal end of a fiber 120 provided within a needle 118 (shown in FIG. 15) that is attached to the base disk 112.

Figure 13A:
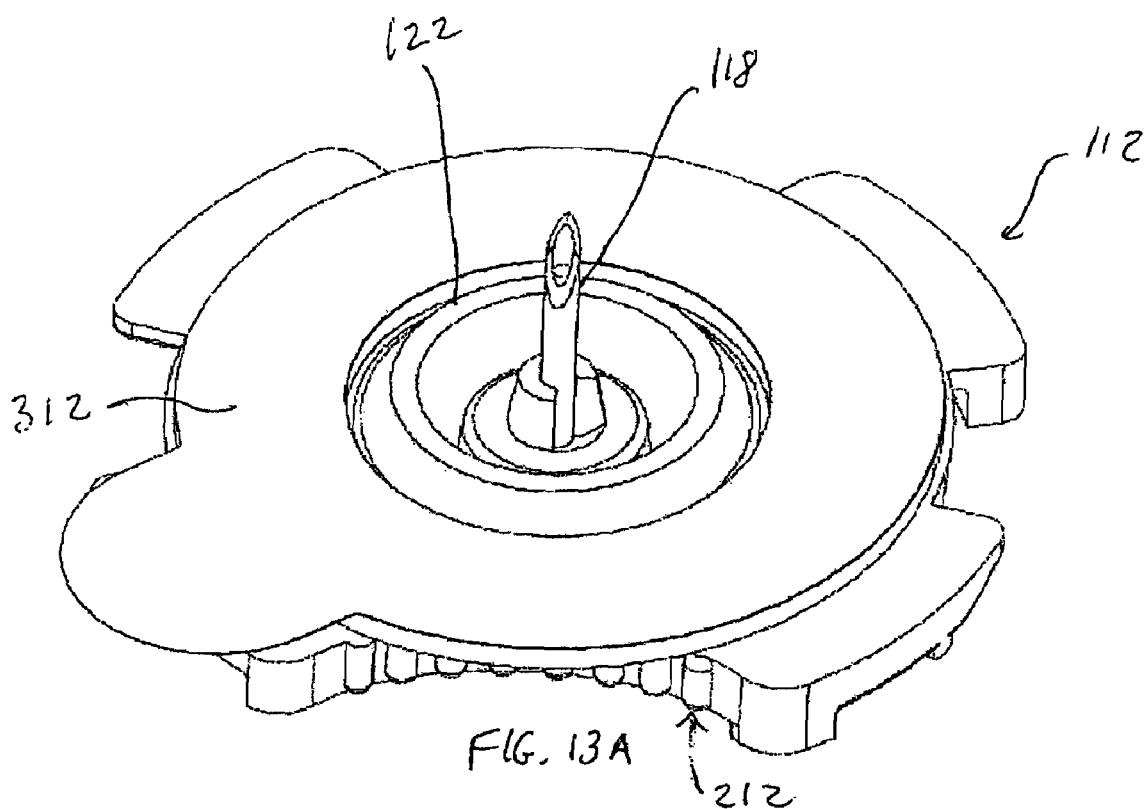
FIGS. 13A-13C show the distal or underside of a base disk of the second exemplary embodiment.
Figure 13B:
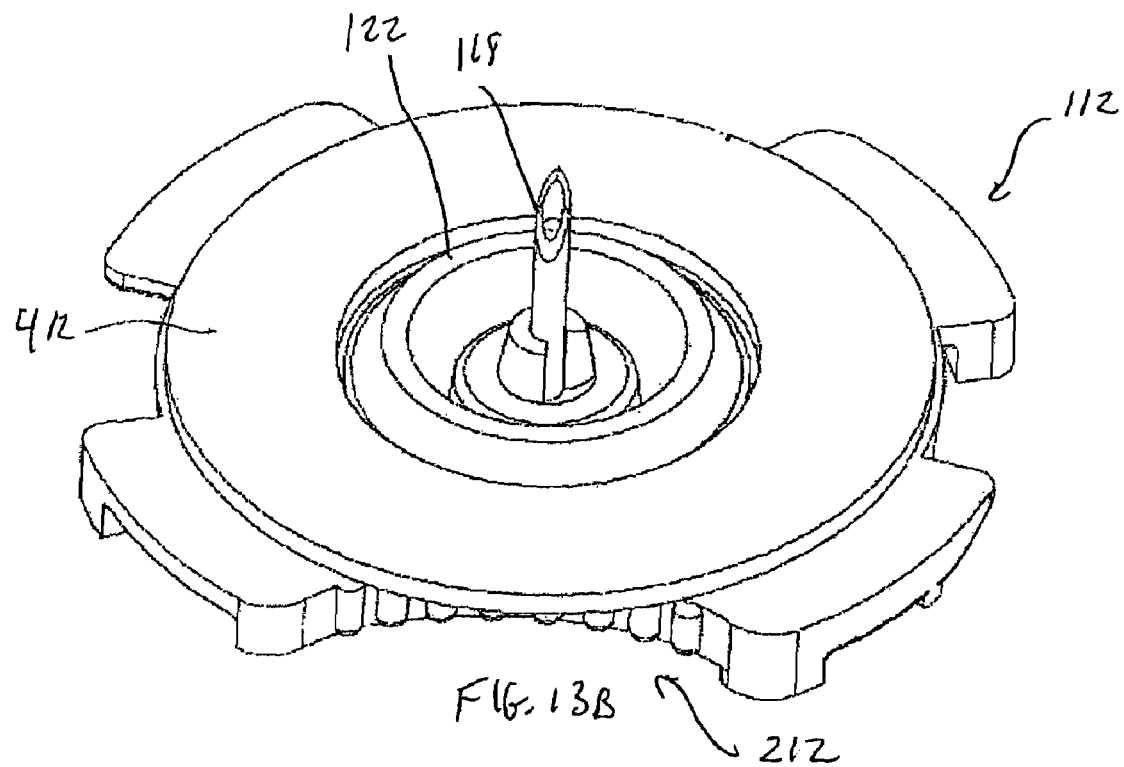
Figure 13C:
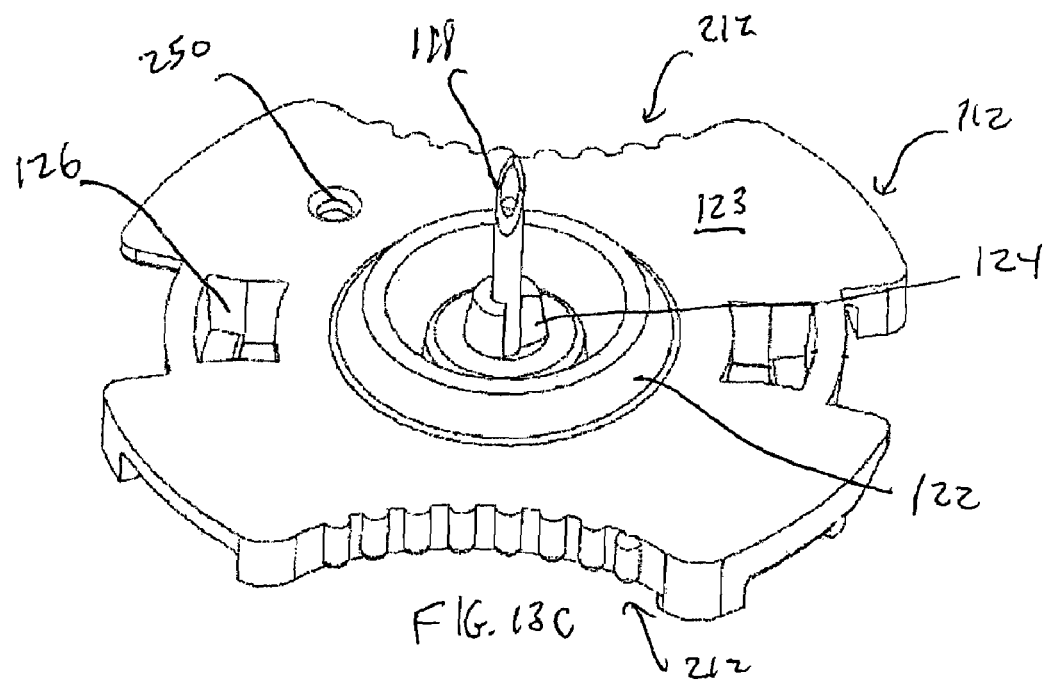

FIGS. 13A-13C show the distal or underside of the base disk 112 of the second exemplary embodiment. As shown in FIG. 13C, in the base disk 112 has a general flat shape with finger gripping portions 212 provided at the disk's perimeter. These finger gripping portions 212 are designed to assist the patient with gripping and positioning the base disk 112. Like the first exemplary embodiment, the base disk 112 of the second exemplary embodiment includes a circular or frustoconical rim 122 spaced radially inward from the perimeter and protruding in a distal direction from a distal surface 123 of disk 112 and a glue well 124 for fixing the needle 118 to the body of disk 112.

As shown in FIGS. 13A and 13B, in this exemplary embodiment a protective liner 312 is provided on an adhesive layer 412. The adhesive layer 412 is designed to secure the disk 112 onto the patient's skin. Accordingly, after the protective liner 312 (FIG. 13A) is removed from the adhesive layer 412 (FIG. 13B), the adhesive layer is ready to be applied to the patient.

FIG. 13B shows the adhesive layer 412 as protruding beyond the periphery of the base disk 112 at the locations of the finger gripping portions 212. However, the adhesive layer 412 can be sized so that it is substantially the same size and/or profile as the periphery of the base disk 112. Alternatively, the portions of a top of the adhesive layer 412 (i.e., the side that contacts the base disk) that extend beyond the periphery of the base disk 112 can have their stickiness or tackiness removed so that only a bottom portion, which is designed to contact the patient's skin, remains tacky.

FIG. 13C shows an alignment hole 250 provided in the lower surface 123 of the base disk 112. This alignment hole 250 assists with the orientation of the base disk during the manufacturing process and does not provide any function in actual operation of the device 100.

Moreover, FIG. 13C shows the interior of receptacles 126, which are designed to be engaged with prongs 142 of the connector 115. That is, as best seen in FIG. 12, the proximal or back side of the base disk 112 generally include receptacles 26 adjacent a central collar portion 128. The receptacles 126 receive and/or accommodate arms 132 of the connector 116.

Figure 14:
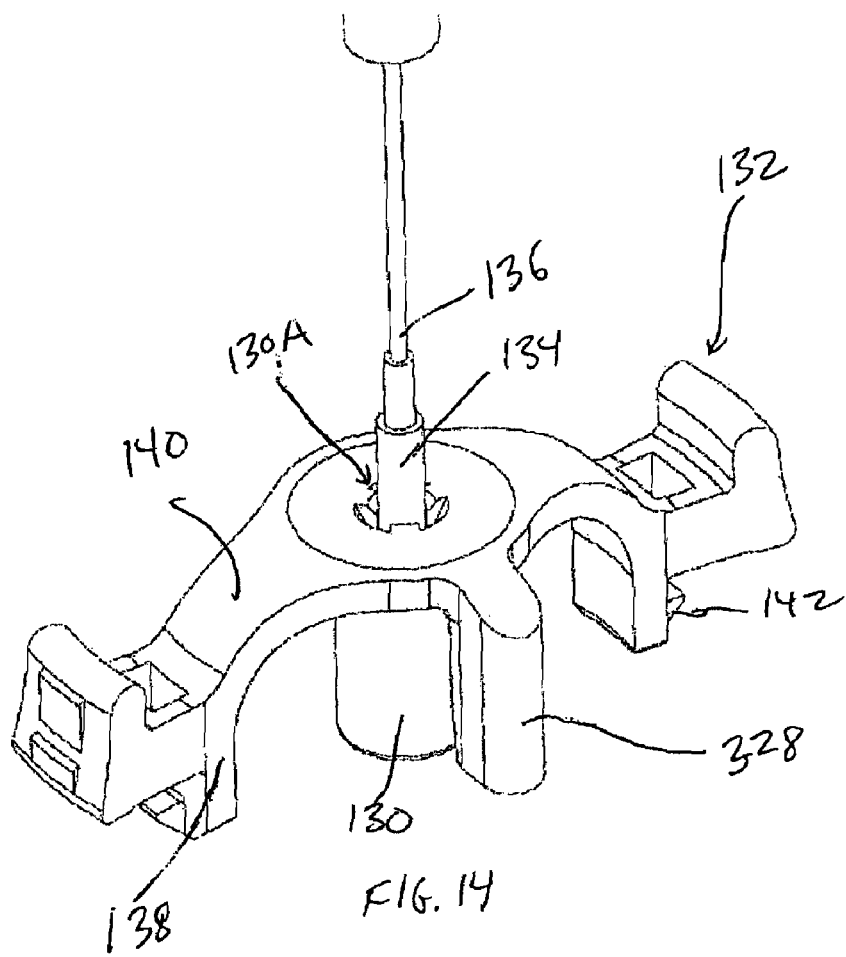
FIG. 14 is a perspective view of a connector of the second exemplary embodiment.

Referring to FIG. 14, the connector 116 generally includes a connector body 130 with a pair of tabs or arms 132 extending laterally therefrom. A tube or cannula 134 extends through connector body 30 and houses a portion of a second fiber 136, which acts as an optical conduit through which light signals may pass. As shown in FIG. 11, in a fiber pigtail 137 may extend from the proximal end of connector 116 so that the fiber 136 can communicate with an external reader (not shown). Like the connector 16 of the first exemplary embodiment, the connector 116 of the second exemplary embodiment has a general U or horseshoe shape with sidewalls 138 extending distally from top wall portion 140. Prong members 142 extend laterally outward from distal ends of sidewalls 138 and are configured and dimensioned to engage a portion of receptacles 126 to snap or hold connector 116 in place with respect to base disk 112. Like the first exemplary embodiment, the arms 132 of the connector 116 of the second exemplary embodiment are generally flexible such that the arms may be squeezed together by a user or pushed downward and radially inward to move the prongs 142 radially inward and provide clearance to insert or remove connector 116 from base disk 112. When the arms 132 are released, the prongs 142 resiliently snap fit into the receptacles 126 on base disk 112 to attach the connector 116 to the base disk 112.

Figure 16:
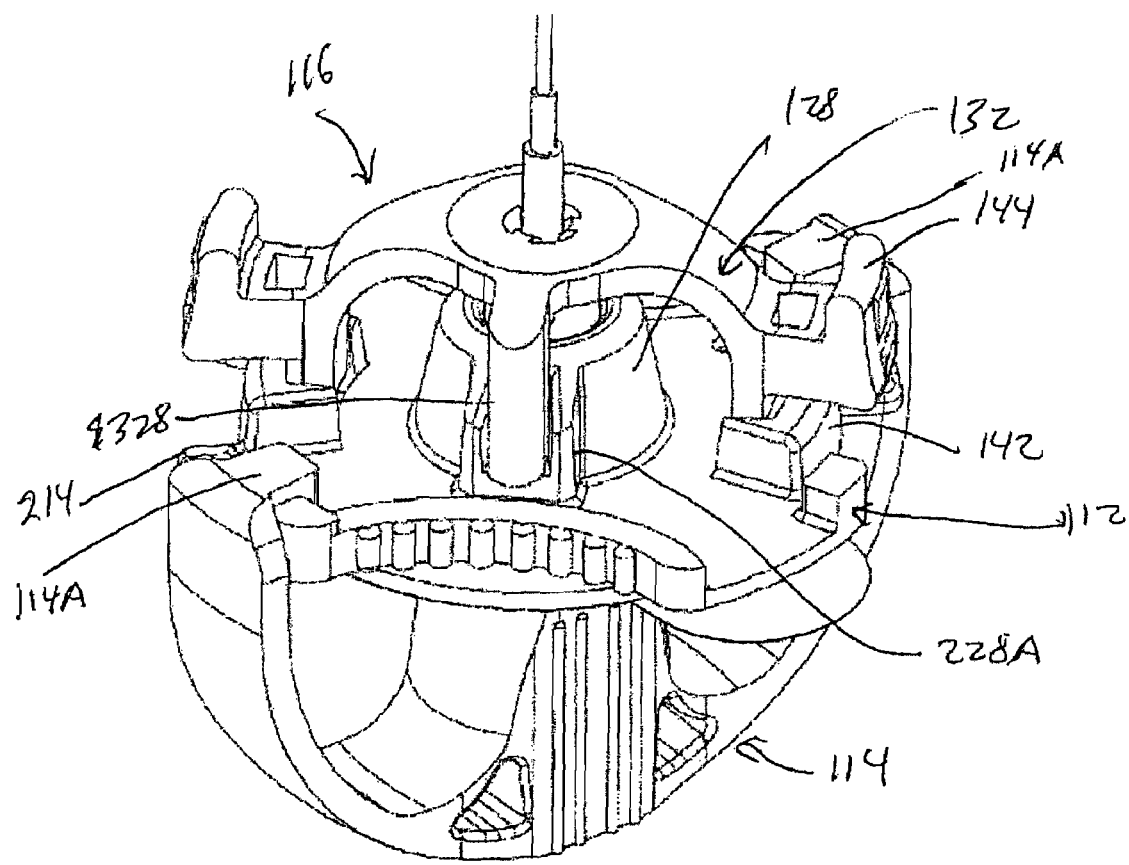
FIG. 16 shows a perspective view of the connector, the base disk, and a cover of the second exemplary embodiment.

As shown in FIG. 14, the connector 116 includes a key feature 328 that extends downward from the top wall portion 140 at only one side of the connector 116. As best shown in FIG. 16, the key feature 328 can be inserted into a corresponding key feature 228A provided at a proximal side, or top, of the base disk 112. The key features 328, 228A align the connector 116 with the disk 112 and prevent relative rotation between the connector 116 and base disk 112. Moreover, this configuration ensures that the connector 116 and base disk 112 can only be engaged in one orientation, which in turn improves repeatability of connection characteristics. That is, the side of the base disk opposing the key feature 228A includes a blocking feature 228B (shown in FIG. 12), which prevents the key feature 328 of the connector 116 from being incorrectly inserted into the base disk 112.

Moreover, the top of the body portion 130 includes chamfers or grooves 130A that assist with the alignment of the cannula 134 when it is inserted into the body 130.

Figure 15:
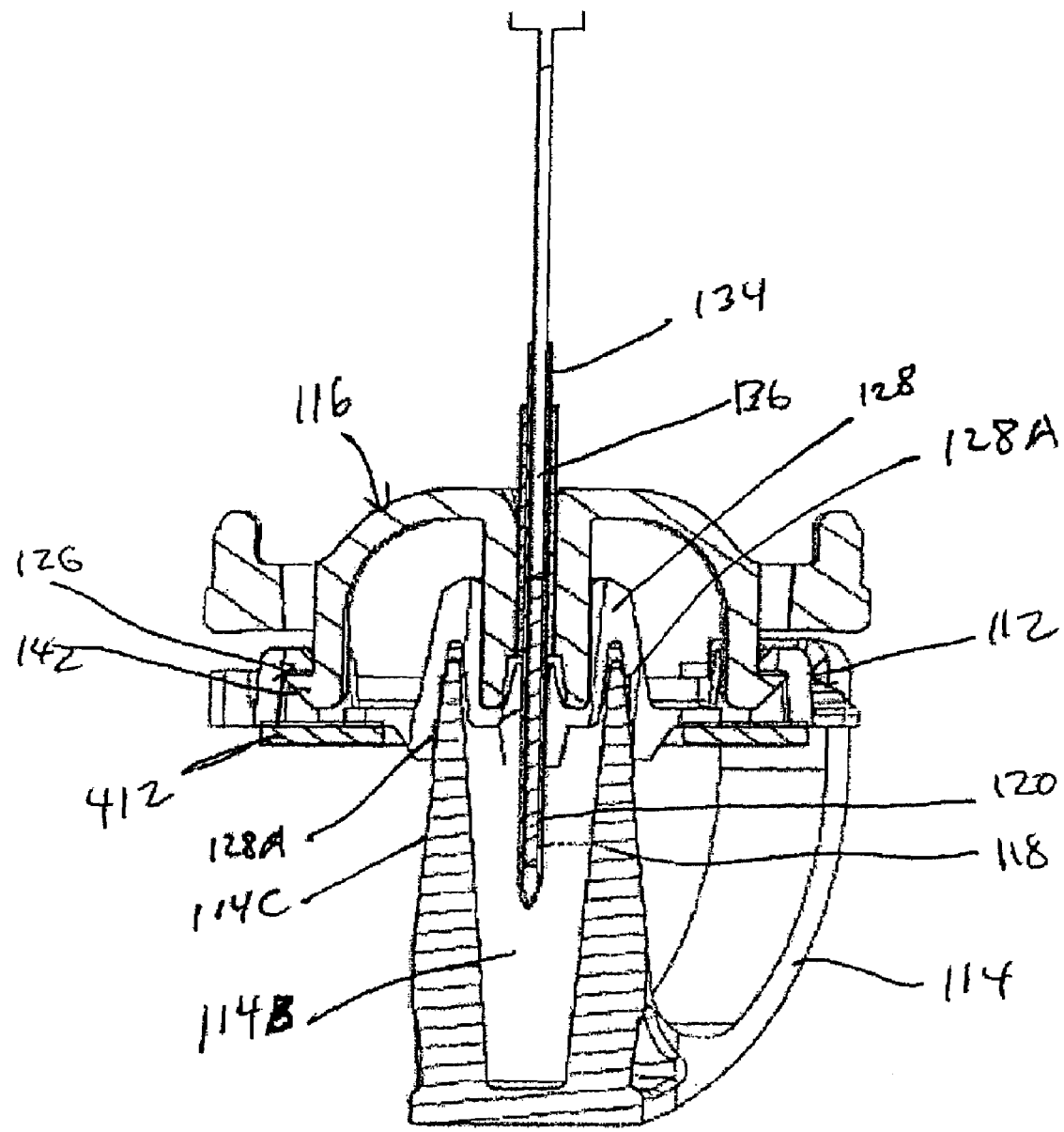
FIG. 15 is a cross-sectional view of the device of the second exemplary embodiment.

FIG. 15 shows a cross-section of the connector 116 engaged with the base disk 112 and the removable cover 114 provided on the base disk 112. The prongs 142 of the connector 116 are engaged with the receptacles of the base disk 112.

FIG. 16 shows a perspective view of the connector 116, base disk 112, and cover 114. The cover 114 includes a hydration chamber 114B that is provided with fluid. The fluid within the hydration chamber 114B protects any chemistry provided at a distal end of the needle 118 and fiber 120.

The engagement between the hydration chamber 114B and the base disk 112 must be sufficient to seal the fluid within the hydration chamber 114B. Accordingly, unlike the engagement between the connector 116 and the base disk 112, the cover 114 is rotatably engaged with the base disk 112. That is, the cover 114 is engaged to the base disk 112 by providing engagement arms 114A of the cover 114 over inclined connection portions 214 provided on the proximal side, or top, of the base disk 112. FIG. 12 best shows the inclined surface of the inclined connection portion 214.

Moreover, as shown in FIG. 15 (and also FIGS. 17A, and 17B), stepped portions 128A within the central collar portion 128 of the base disk provide a good seal with the outer surface 114C of the hydration chamber 114B.

Figure 17A:
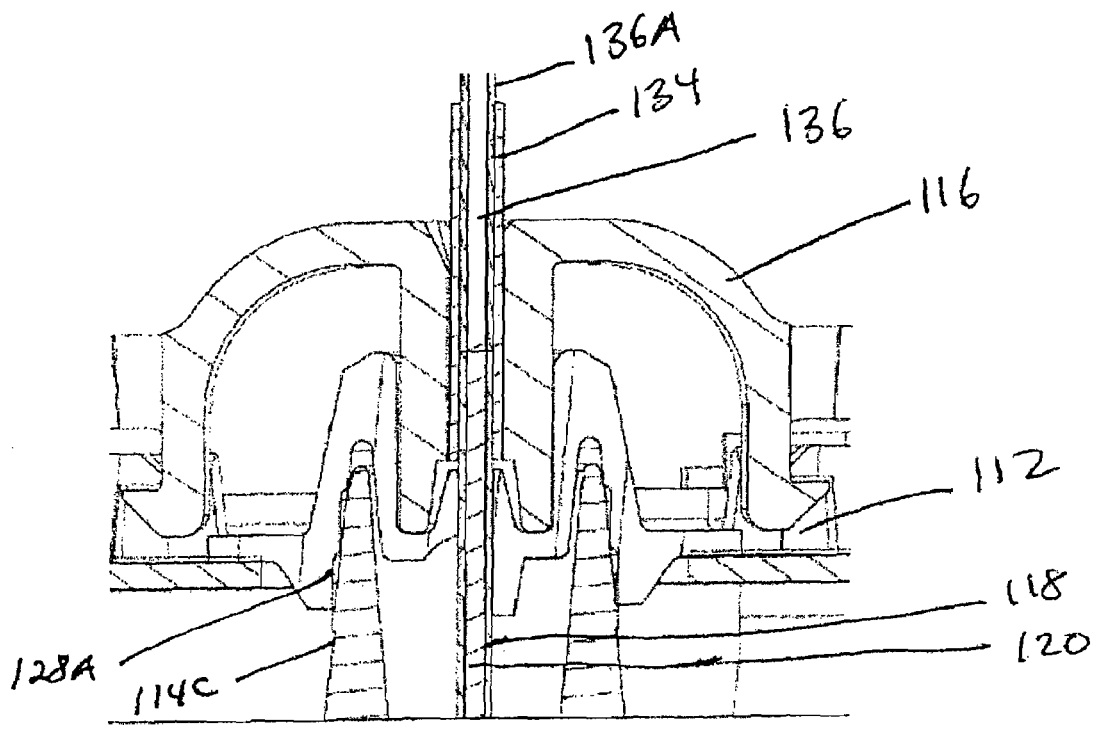
FIGS. 17A and 17B are enlarged cross-sectional views of the device of the second exemplary embodiment and a modification thereof, respectively.
Figure 17B:
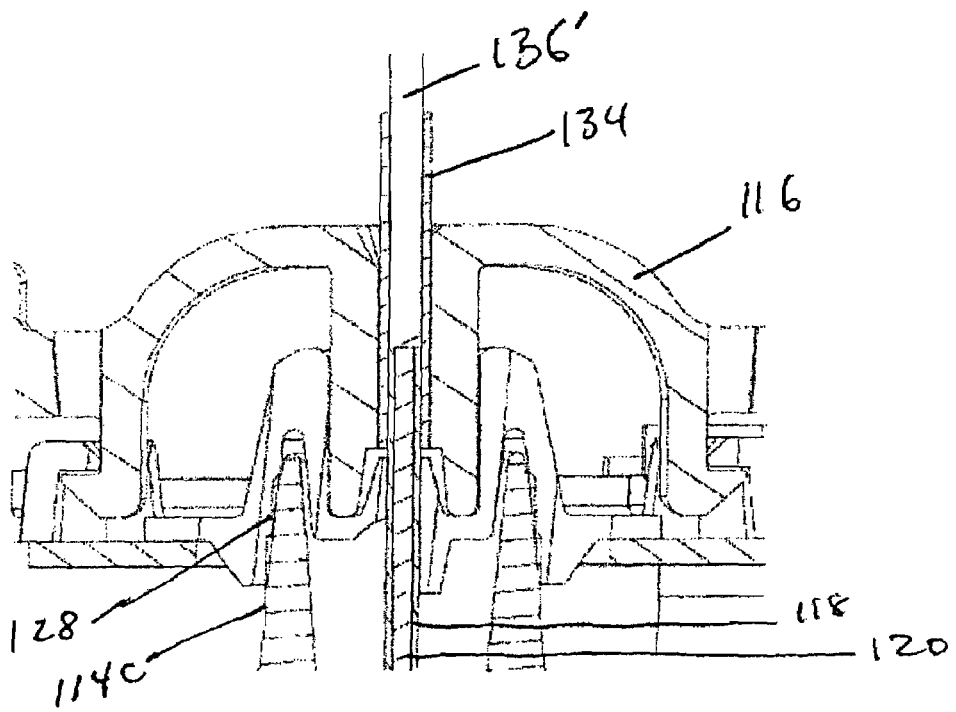

FIGS. 17A and 17B are enlarged cross-sectional views of the optical fiber connection of the device 100 of the second exemplary embodiment and a modification thereof, respectively. That is, FIG. 17A shows detail of the connection between the insertable fiber 120 (within the needle 118) of the base disk 112 and the fiber 136 of the connector 116 (within the cannula 134). In this exemplary embodiment, the 200 um fiber 136 includes an 25 Ga inner cannula (or bushing) 136A that is provided within the 21 Ga cannula 134. Accordingly, the 25 Ga inner cannula 136A can match the size of the 25 Ga needle 118. Using this structure, two 200 um fibers can be aligned. The force of engagement between connector 116 and the base disk 112 can bring the fibers 120, 136 into contact. Alternatively, a small gap can be provided between the fibers 120, 136. If a small gap is provided, an index matching gel is provided between the fibers 120, 136.

In contrast, FIG. 17B shows detail of the connection between the 200 um insertable fiber 120 within the 25 Ga needle 118 and a larger 400 um fiber 136' provided within the 21 Ga cannula 134. Using this structure, a 400 um fiber of the connector 116 can be aligned with the 200 um fiber of the base disk 112. This connection could be provided by decoupling the connector 116 shown in FIG. 17A from the base disk 112 and instead coupling the connector 116 shown in FIG. 17B to the base disk 112. By using this combination of 18 Ga and 21 Ga cannula, a 400 um to 400 um fiber coupling can be accomplished as described above.

While the invention herein disclosed has been described by means of exemplary embodiments and applications thereof, numerous modifications and variations can be made thereto by those skilled in the art without departing from the scope of the invention.

What is claimed is:

1. An optical connector device for optically connecting a biosensor wearable on a body of a patient to a reader outside of the body, comprising:
a base disk configured and dimensioned to be worn on the body of a patient, the base disk having a needle attached thereto, the needle housing a first fiber defining a first optical conduit, wherein the needle comprises a proximal end and a distal end, wherein the distal end of the needle is insertable into the body of the patient and is configured to remain inside of the body of the patient with at least a portion of the proximal end of the needle remaining outside of the body of the patient when the device is worn, wherein a generally circular rim is spaced radially inward from the perimeter and protrudes in a distal direction from the distal side of the base disk; and
a connector housing a second fiber defining a second optical conduit, wherein the connector is configured and dimensioned to couple with the base disk to position the first fiber in optical proximity to the second fiber and align the first optical conduit with the second optical conduit such that an optical signal may be transmitted from the first optical conduit to the second optical conduit.

2. The device of claim 1, wherein a sensor element is positioned on the distal end of the needle and the sensor element is configured to transmit an optical signal in response to a target analyte.

3. The device of claim 2, further comprising a removable cover positionable over the distal end of the needle for protecting the sensor element when not in use.

4. The device of claim 3, wherein the cover comprises a hydration chamber to keep the sensor element wet.

5. The device of claim 1, wherein the connector is removably coupleable to the base disk.

6. The device of claim 1, further comprising a depth limiting device attached to the base disk wherein the depth limiting device limits the depth that the distal end of needle may be inserted into the body of the patient.

7. The device of claim 1, wherein the base disk comprises an adhesive configured and dimensioned to be worn on the exterior skin of the patient.

8. The device of claim 1, wherein the base disk comprises a distal side and a proximal side and the distal side is configured to contact the exterior skin of the patient, and wherein base disk has a general flat shape with a generally circular perimeter.

9. The device of claim 1, wherein the needle fixed to the base disk with glue and a glue well is positioned on the distal side of the base disk to fix the needle to the base disk.

10. The device of claim 1, wherein at least one receptacle is positioned on the proximal side of the base disk to receive at least a portion of the connector.

11. The device of claim 10, wherein the connector further comprises a connector body with a pair of arms extending laterally therefrom.

12. The device of claim 11, wherein the connector body has a general U shape with sidewalls extending distally from a top wall portion.

13. The device of claim 12, further comprising at least one prong member extending laterally outward from the sidewalls, wherein the prong member is configured and dimensioned to engage a portion of the receptacle to mate the connector with respect to the base disk.

14. The device of claim 13, wherein a portion of the pair of arms are sloped downward.

15. The device of claim 14, wherein the arms are generally flexible such that the arms may be squeezed together by a user to insert or remove the connector from the base disk.

16. The device of claim 1, wherein the base disk has a height between about 0.1 cm and about 2 cm.

17. The device of claim 1, further comprising a fiber pigtail extending from the proximal end of the connector.

18. The device of claim 1, wherein the connector is integrally formed with a wearable optic reader.

19. The device of claim 1, wherein when the connector is coupled to the base disk, the connector is resiliently biased against the base disk to hold the first and second fibers in close proximity.

20. The device of claim 1, wherein the base disk and connector are made from plastic.

21. The device of claim 1, wherein the total height of the device is less than about 1 cm.

22. The device of claim 1, wherein the first optical conduit has a first diameter and the second optical conduit has a second diameter and wherein the first and second diameters are substantially the same size.

23. The device of claim 1, wherein the first optical conduit has a first diameter and the second optical conduit has a second diameter and wherein the first and second diameters are different sizes.

24. The device of claim 1, wherein the connector is keyed to align with the base disk to prevent relative rotation between the connector and base disk upon coupling.

25. A method of optically connecting a biosensor wearable on a body of a patient to a reader outside of the body, comprising: (a) attaching the optical connector device of claim 1 to the body of the patient such that the needle is inserted into the body of the patient and (b) coupling the connector of the optical connector with the base disk of the optical connector.

26. The method of claim 25, further comprising decoupling the connector from the base disk, and coupling another connector to the base disk.

27. The method of claim 25, wherein the attaching the optical connector to the body of the patient includes inserting the distal end of the needle such that the needle is substantially perpendicular to the patient's skin.

28. The method of claim 27, wherein the coupling of the connector to the base disk includes aligning the connector so that the second fiber is substantially aligned with respect to the first fiber.

29. The method of claim 25, wherein the coupling of the connector to the base disk includes aligning the connector so that a center of the connector is provided over a center of the base disk.

30. The method of claim 25, wherein the attaching the optical connector to the body of the patient includes inserting the distal end of the needle such that the needle is substantially perpendicular to the patient's skin.

31. An optical connector device for optically connecting a biosensor wearable on a body of a patient to a reader outside of the body, comprising:
a base disk configured and dimensioned to be worn on the body of a patient, the base disk having a needle attached thereto, the needle housing a first fiber defining a first optical conduit, wherein the needle comprises a proximal end and a distal end, wherein the distal end of the needle is insertable into the body of the patient and is configured to remain inside of the body of the patient with at least a portion of the proximal end of the needle remaining outside of the body of the patient when the device is worn, wherein a sensor element is positioned on the distal end of the needle and the sensor element is configured to transmit an optical signal in response to a target analyte,
a removable cover comprising a hydration chamber and positionable over the distal end of the needle, and
a connector housing a second fiber defining a second optical conduit, wherein the connector is configured and dimensioned to couple with the base disk to position the first fiber in optical proximity to the second fiber and align the first optical conduit with the second optical conduit such that an optical signal may be transmitted from the first optical conduit to the second optical conduit.

32. The device of claim 31, wherein the connector is removably coupleable to the base disk.

33. The device of claim 31, further comprising a depth limiting device attached to the base disk wherein the depth limiting device limits the depth that the distal end of needle may be inserted into the body of the patient.

34. The device of claim 31, wherein the base disk comprises an adhesive configured and dimensioned to be worn on the exterior skin of the patient.

35. The device of claim 31, wherein the base disk has a height between about 0.1 cm and about 2 cm.

36. The device of claim 31, wherein the connector is integrally formed with a wearable optic reader.

37. The device of claim 31, wherein the base disk and connector are made from plastic.

38. The device of claim 31, wherein the first optical conduit has a first diameter and the second optical conduit has a second diameter and wherein the first and second diameters are substantially the same size.

39. The device of claim 31, wherein the first optical conduit has a first diameter and the second optical conduit has a second diameter and wherein the first and second diameters are different sizes.

40. The device of claim 31, wherein the connector is keyed to align with the base disk to prevent relative rotation between the connector and base disk upon coupling.

41. A method of optically connecting a biosensor wearable on a body of a patient to a reader outside of the body, comprising: (a) attaching the optical connector device of claim 31 to the body of the patient such that the needle is inserted into the body of the patient, and (b) coupling the connector of the optical connector with the base disk of the optical connector.

42. An optical connector device for optically connecting a biosensor wearable on a body of a patient to a reader outside of the body, comprising:
a base disk having a proximal side and a distal side and configured and dimensioned to be worn on the body of a patient, the base disk having a needle attached thereto, the needle housing a first fiber defining a first optical conduit, wherein the needle comprises a proximal end and a distal end, wherein the distal end of the needle is insertable into the body of the patient and is configured to remain inside of the body of the patient with at least a portion of the proximal end of the needle remaining outside of the body of the patient when the device is worn, wherein at least one receptacle is positioned on the proximal side of the base disk to receive at least a portion of the connector,
a connector housing a second fiber defining a second optical conduit, wherein the connector comprises a connector body with a pair of arms extending laterally therefrom and is configured and dimensioned to couple with the base disk to position the first fiber in optical proximity to the second fiber and align the first optical conduit with the second optical conduit such that an optical signal may be transmitted from the first optical conduit to the second optical conduit.

43. The device of claim 42, wherein the connector is removably coupleable to the base disk.

44. The device of claim 42, further comprising a depth limiting device attached to the base disk wherein the depth limiting device limits the depth that the distal end of needle may be inserted into the body of the patient.

45. The device of claim 42, wherein the base disk comprises an adhesive configured and dimensioned to be worn on the exterior skin of the patient.

46. The device of claim 42, wherein the base disk has a height between about 0.1 cm and about 2 cm.

47. The device of claim 42, wherein the connector body has a general U shape with sidewalls extending distally from a top wall portion.

48. The device of claim 47, further comprising at least one prong member extending laterally outward from the sidewalls, wherein the prong member is configured and dimensioned to engage a portion of the receptacle to mate the connector with respect to the base disk.

49. The device of claim 42, wherein the arms are generally flexible such that the arms may be squeezed together by a user to insert or remove the connector from the base disk.

50. The device of claim 42, wherein the base disk and connector are made from plastic.

51. The device of claim 42, wherein the first optical conduit has a first diameter and the second optical conduit has a second diameter and wherein the first and second diameters are substantially the same size.

52. The device of claim 42, wherein the first optical conduit has a first diameter and the second optical conduit has a second diameter and wherein the first and second diameters are different sizes.

53. The device of claim 42, wherein the connector is keyed to align with the base disk to prevent relative rotation between the connector and base disk upon coupling.

54. A method of optically connecting a biosensor wearable on a body of a patient to a reader outside of the body, comprising: (a) attaching the optical connector device of claim 42 to the body of the patient such that the needle is inserted into the body of the patient, and (b) coupling the connector of the optical connector with the base disk of the optical connector.

55. The method of claim 54, wherein the attaching the optical connector to the body of the patient includes inserting the distal end of the needle such that the needle is substantially perpendicular to the patient's skin.

56. An optical connector device for optically connecting a biosensor wearable on a body of a patient to a reader outside of the body, comprising:
  a base disk configured and dimensioned to be worn on the body of a patient, the base disk having a needle attached thereto, the needle housing a first fiber defining a first optical conduit, wherein the needle comprises a proximal end and a distal end, wherein the distal end of the needle is insertable into the body of the patient and is configured to remain inside of the body of the patient with at least a portion of the proximal end of the needle remaining outside of the body of the patient when the device is worn, and
  a connector housing a second fiber defining a second optical conduit, wherein the connector is configured and dimensioned to couple with the base disk to position the first fiber in optical proximity to the second fiber and align the first optical conduit with the second optical conduit such that an optical signal may be transmitted from the first optical conduit to the second optical conduit, and wherein the connector is integrally formed with a wearable optic reader.

57. The device of claim 56, wherein a sensor element is positioned on the distal end of the needle and the sensor element is configured to transmit an optical signal in response to a target analyte.

58. The device of claim 56, wherein the connector is removably coupleable to the base disk.

59. The device of claim 56, further comprising a depth limiting device attached to the base disk wherein the depth limiting device limits the depth that the distal end of needle may be inserted into the body of the patient.

60. The device of claim 56, wherein the base disk comprises an adhesive configured and dimensioned to be worn on the exterior skin of the patient.

61. The device of claim 56, wherein the base disk has a height between about 0.1 cm and about 2 cm.

62. The device of claim 56, wherein the base disk and connector are made from plastic.

63. The device of claim 56, wherein the first optical conduit has a first diameter and the second optical conduit has a second diameter and wherein the first and second diameters are substantially the same size.

64. The device of claim 56, wherein the first optical conduit has a first diameter and the second optical conduit has a second diameter and wherein the first and second diameters are different sizes.

65. The device of claim 56, wherein the connector is keyed to align with the base disk to prevent relative rotation between the connector and base disk upon coupling.

66. A method of optically connecting a biosensor wearable on a body of a patient to a reader outside of the body, comprising: (a) attaching the optical connector device of claim 56 to the body of the patient such that the needle is inserted into the body of the patient, and (b) coupling the connector of the optical connector with the base disk of the optical connector.

67. The method of claim 66, wherein the attaching the optical connector to the body of the patient includes inserting the distal end of the needle such that the needle is substantially perpendicular to the patient's skin.

* * * * *

UNITED STATES PATENT AND TRADEMARK OFFICE
CERTIFICATE OF CORRECTION

PATENT NO. : 8,369,916 B2  Page 1 of 1
APPLICATION NO. : 12/527999
DATED : February 5, 2013
INVENTOR(S) : Jacobson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 686 days.

Signed and Sealed this

First Day of September, 2015

Michelle K. Lee
*Director of the United States Patent and Trademark Office*